United States Patent [19]

Helfer

[11] Patent Number: 4,857,054

[45] Date of Patent: Aug. 15, 1989

[54] PERFUSION ANGIOPLASTY CATHETER WITH PUMP ASSIST

[75] Inventor: Jeffrey L. Helfer, Webster, N.Y.

[73] Assignee: Eastman Kodak Company, Rochester, N.Y.

[21] Appl. No.: 219,526

[22] Filed: Jul. 15, 1988

[51] Int. Cl.[4] .......................................... A61M 75/00
[52] U.S. Cl. .................................. 604/102; 604/247; 128/344
[58] Field of Search ...................... 604/27, 35, 36, 38, 604/96–102, 247, 9; 128/344

[56] References Cited

U.S. PATENT DOCUMENTS

| 3,592,184 | 7/1971 | Watkins et al. |
| 3,889,686 | 6/1975 | Duturbure ............................ 604/102 |
| 3,923,065 | 12/1975 | Nozick et al. ......................... 604/102 |
| 4,213,461 | 7/1980 | Pevsner . |
| 4,407,271 | 10/1983 | Schiff . |
| 4,445,892 | 5/1984 | Hussein et al. |
| 4,471,779 | 9/1984 | Antoshkiw et al. |
| 4,581,017 | 4/1986 | Sahota . |
| 4,610,662 | 9/1986 | Weikl et al. |
| 4,646,742 | 3/1987 | Packard et al. |
| 4,657,536 | 4/1987 | Dorman ................................. 604/9 |
| 4,666,426 | 5/1987 | Aigner . |
| 4,753,640 | 6/1988 | Nichols et al. ...................... 604/247 |

FOREIGN PATENT DOCUMENTS 192575 2/1986 European Pat. Off. .

Primary Examiner—Stephen C. Pellegrino
Attorney, Agent, or Firm—Dana M. Schmidt

[57] ABSTRACT

A catheter is described to provide perfusion while a body vessel is being blocked by the catheter for angioplasty treatment. Intake apertures and ejection apertures are constructed with one-way valves that permit the upstream apertures to only take fluid into the catheter, and the downstream apertures only to eject fluid from the catheter. A pump cooperates with the one-way valves to eject the drawn in aliquot without having to circulate the body fluid outside of the body vessel.

11 Claims, 4 Drawing Sheets

PERFUSION ANGIOPLASTY CATHETER WITH PUMP ASSIST

FIELD OF THE INVENTION

This invention relates to perfusion catheters used in conjunction with the treatment of vessels in a mammalian body, such as blood vessels and the like.

BACKGROUND OF THE INVENTION

Catheters are commonly used invasively to treat diseased vessels in mammalian, and particularly human, bodies. Cardiovascular diseases are one of the most common diseases treated in this fashion, wherein the catheters are used to counter atherosclerosis through such angioplasty treatment modalities as balloon angioplasty. Other uses include: treatment of the urinary tract, brain, lungs, kidneys and/or liver. Such angioplasty treatments of body vessels can include laser cutting, dilation, tissue heating, chemical dissolution of tissues and/or removal of tissue samples.

In some of these treatments, it is contraindicated to have a long-term blockage, that is, one occurring for more than approximately 30-60 seconds. In addition, certain heart-attach victims may have enough necrotic heart tissue that no interruption of blood flow can be safely tolerated. For this reason, perfusion catheters have been constructed which are adapted to pass blood through the catheter even though the catheter is acting to block flow externally of the catheter. That is, balloons are commonly used to dilate partially blocked arteries and veins to restore more normal blood flow. It has been found that the dilation is more effective if prolonged; yet this usually means a prolonged blockage of flow around the catheter since the balloon of the catheter fills the body vessel.

Conventional perfusion catheters have one or more simple apertures upstream of the blockage site, and one or more downstream. See for example, U.S. Pat. No. 4,581,017, FIG. 2. Such catheters have a rate of flow-through that is primarily controlled by the diameter of the flow lumens within the catheter and the pressure difference across the lumens. The magnitude of that rate does not usually provide the high fluid flow rate required of that body vessel. As a result, treatments requiring a more extended blockage are risky, since even with the perfusion provided, the flow downstream of the catheter is not equal to natural flow.

In dealing with the aforesaid problem, pumps have been hooked up to perfusion catheters. However, as shown for example in U.S. Pat. No. 4,666,426, the approach has been to withdraw blood from apertures at an upstream location, deliver it to the pump itself and to processing stations located ex vivo, and then return it to the catheter to be expelled back into the body vessel at apertures located downstream of the intake apertures. Such an arrangement requires the blood to run the complete circuit, including ex vivo stations. This creates the following problems:

(1) There is greater risk of contamination to the patient as well as attendants, since blood contactable objects are not confined with the body.

(2) Such a system is more likely to lyse blood cells due to the greater exposure to potentially "unnaturally high" fluid shear stresses encountered within the pumping system.

(3) The pumping system is not entirely disposable. The parts not disposable must be cleaned, which is an expense that should be avoided.

Thus, a first problem prior to this invention has been to provide a higher throughput of body fluids in a perfusion catheter, so as to allow a more prolonged obstruction of the vessel carrying the fluid, by the catheter.

A second problem prior to the invention has been to provide a perfusion catheter and pump arrangement wherein the blood or other body fluid is drawn into the catheter, bypassing the obstruction, and then immediately expelled under pressure, without undergoing an extensive ex vivo loop.

SUMMARY OF THE INVENTION

I have developed a perfusion catheter that avoids the aforementioned problems by providing a high-rate of flow-through. This is accomplished through the use of a pump that, because of the construction of the distal end apertures, does not require the body fluids to circulate ex vivo.

More specifically, in accord with one aspect of the invention there is provided a perfusion angioplasty catheter comprising a tube having a distal end including means for effecting angioplasty treatment of a body vessel, and a proximal end containing control means, the tube further comprising at least a perfusion lumen extending most of the length of the tube, and means in the tube adjacent the distal end, defining a plurality of apertures providing for fluid movement from or to the lumen, to or from a body vessel. This catheter is improved in that it further comprises a plurality of one-way valves, each disposed at one of the apertures, at least one of the valves being constructed to admit fluid only into the lumen from a body vessel, and at least one other of the valves being constructed to admit fluid only to a body vessel from the lumen.

In accord with another aspect of the invention, there is provided a perfusion angioplasty catheter for insertion into a vessel of a mammalian body, the catheter comprising a distal end including treating means for effecting angioplasty treatment of a body vessel, a proximal end that remains outside of the body vessel, and a body portion extending between and connecting the ends, the distal end being provided with at least one lumen and at least one aperture on either side of the treating means, constructed to allow flow into and out of the catheter from and to, respectively, a body vessel. This catheter is improved in that the distal end further includes a plurality of one-way valves, each disposed at one of the apertures, at least one of said valves being constructed to admit fluid only into the lumen from a body vessel, and at least one other of the valves being constructed to admit fluid only to a body vessel from the lumen.

In accord with yet another aspect of the invention, there is provided a perfusion angioplasty catheter for insertion into a vessel of a mammalian body, the catheter comprising a distal end including treating means for effecting angioplasty treatment of a body vessel, a proximal end that remains outside of the body vessel, and a body portion extending between and connecting the ends. The catheter is improved in that it further includes means for drawing fluid into a catheter from the body vessel only at location in said distal end that are upstream of said treating means when the catheter is in place in a body vessel, means for expelling fluid from the catheter under pressure in excess of approximately 120 mm of Hg only at locations in said distal end that are downstream of said treating means when the catheter is in place in a body vessel; and means for transferring indrawn fluid from said upstream locations to said downstream locations and to the exterior of the catheter without withdrawing said indrawn fluid out of the body vessel from which the fluid was taken.

Thus, it is an advantageous feature of this invention that a perfusion catheter is provided having an improved throughput rate, thus allowing treatments with the catheter of this invention that require longer blockage of the body vessel by the catheter, than has heretofore been possible.

It is a further advantageous feature of this invention that a perfusion catheter is provided that does not require the body fluid being perfused, to take a circuit out of the body vessel.

Other advantageous features will become apparent upon reference to the detailed description of the preferred embodiments, when read in light of the attached drawings.

DESCRIPTION OF THE PREFERRED EMBODIMENTS

The invention is described hereinafter with respect to angioplasty treatment in an artery, wherein blood is the perfused body fluid, using a disposable catheter. In addition, it is applicable to any angioplasty treatment in any body vessel in which liquid needs to be perfused at a high throughput rate, whether or not the catheter is disposable.

As used herein, "angioplasty treatment" refers to any technique for increasing the cross-sectional area of a body vessel. Catheters providing such treatment are considered to be in a class by themselves, and different from other kinds of catheters such as aortic assist catheters.

Figure 1:
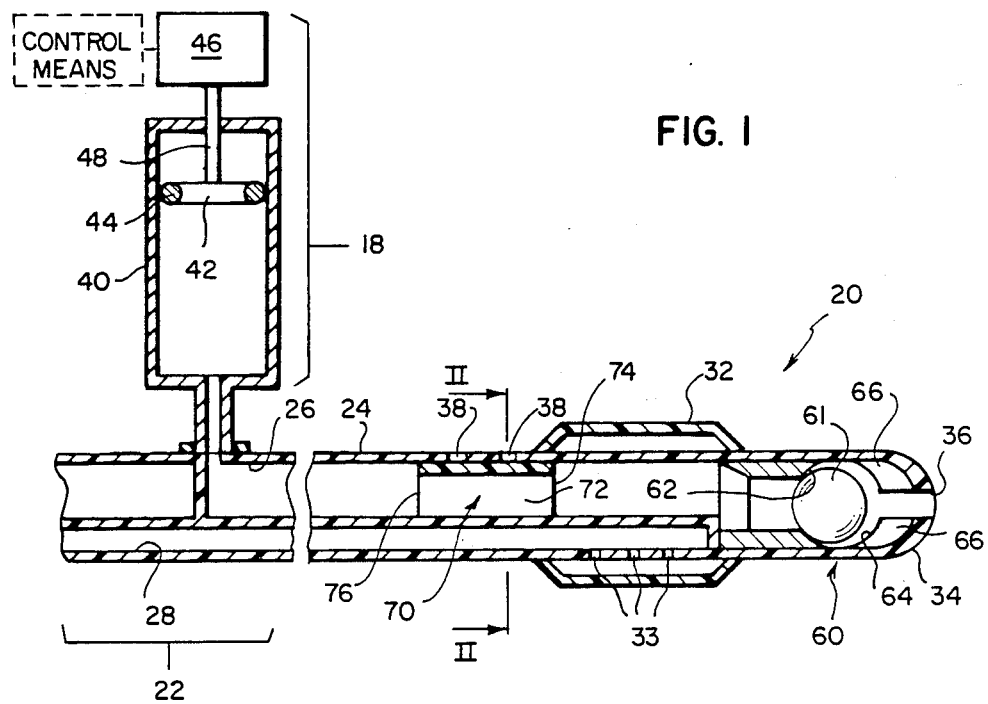
FIG. 1 is a fragmentary longitudinal sectional view through a catheter constructed in accordance with the invention, taken generally along the line I—I of FIG. 2.
Figure 2:
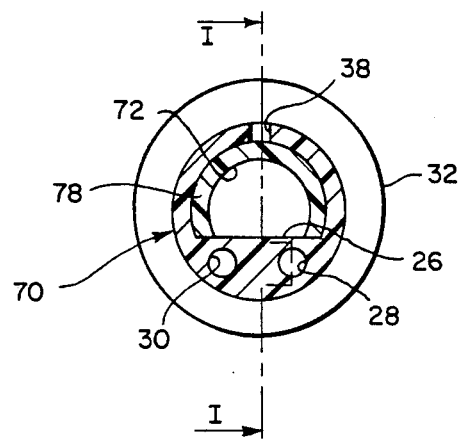
FIG. 2 is a transverse section view taken generally along the line II—II of FIG. 1.

A cathether 10 constructed in accordance with the invention comprises, FIGS. 1-2, distal end 20 constructed to travel within a body vessel and a proximal end 22 constructed to remain ex vivo. The two ends 20 and 22 are connected by a tube 24 defining the body portion of the catheter. Tube 24 is highly flexible, and encloses at least a perfusion lumen 26 that extends from proximal end 22 to distal end 20 via tube 24. Preferably, it also encloses at least one, and most preferably, two additional lumens 28 and 30, FIG. 2. As shown, lumens 28 and 30 both are used to inflate and deflate balloon(s) 32 via apertures 33, as is conventional, located at distal end 20. The balloon(s) are effective to treat the blood vessel, by pushing build-ups back against the wall of the vessel. (As shownin FIGS. 1 and 2, balloon(s) 32 are only partially inflated.) Alternatively, one or both of lumens 28 and 30 are used to effect other conventional treatments at distal end 20 (not shown), for example to deliver laser light to an illuminating surface, to deliver a control wire for bending the distal end to make course corrections, and the like.

Further as is conventional, lumen 26 extends, FIG. 1, all the way to the distal-most end 34 of the catheter, where it terminates at at least one aperture 36 that is distal to balloon(s) 32. In addition, at least one, and preferably a plurality of other apertures 38 are provided in lumen 26, providing access to the lumen from the exterior of the catheter, at locations that are more proximal than balloon(s) 32. As will become apparent, in use, apertures 38 are upstream of balloon(s) 32, regarding the normal flow of body fluid past or through the catheter, whereas aperture 36 is located downstream.

At proximal end 22, pumping means 18 comprises preferably a piston chamber 40, a piston 42 that reciprocates therein as sealed by O-rings 44, and drive means 46 that drives piston rod 48 and piston 42 under the influence of control means 16, all as is conventional. The operating fluid pushed by piston 42 is preferably an isotonic saline solution, although variations can occur as dictated by the intended use of the catheter. For example, a blood substitute can be used.

Pumping means 18 is connected to lumen 26 by conventional means, shown schematically in FIG. 1 as a collar.

The remainder of proximal end 22 extends to conventional control means, not shown, for controlling the operations of the catheter. Such operations include the inflation and deflation of the balloon, the steering and the advancing/retracting of the catheter, and any other treatments possible using lumens 26, 28 and 30.

In accord with one aspect of the invention, one-way valves 60 and 70 are provided at aperture 36 and apertures 38. These valves act to insure that body fluid is admitted only into lumen 26 from a body vessel at apertures 38, and only out of lumen 26 to the body vessel, at aperture 36.

More specifically, a useful one-way valve for aperture 36 is a ball valve 60 comprising a ball 61 that cooperates with closure seat 62 to completely stop flow of fluid back into lumen 26 from aperture 36. However, a ball run 64 is provided from seat 62 to a point adjacent to aperture 36. The run has two or more passageways 66 that conduct body fluid out of aperture 36 even when ball 61 is adjacent to aperture 36.

The other one-way valve 70 is preferably a flap valve comprising a hemicylinder 72 fitted into lumen 26 underneath apertures 38, and anchored at end 74 to the entire circumference (not shown) of lumen 26. Opposite end 76, however, is free to fold away from lumen 26, at top edge 78, FIG. 2, when a differential inward pressure exits at apertures 38. If a differential outward pressure occurs, or the pressures are generally equal, valve 70 completely closes off apertures 38.

The perfusion operation of catheter 10 will be readily apparent from the preceding. As shown more specifically in FIGS. 3-6, when piston 42 and rod 48 are in the fully extended position, FIG. 3, a previously drawn in aliquot of fluid has been mostly ejected out of aperture 36, arrows 80, because ball 61 is forced away from its seat 62. (The previous aliquot is depicted by empty circles.) The pressure for ejecting this aliquot comes from the injection into the distal end, of the isotonic saline solution "S" (shown as speckled), which otherwise remains solely in tube 24 and the proximal end. Flap valve 70 closes off apertures 38 to prevent the fluid, e.g., blood, from exiting upstream of balloon(s) 32, now fully inflated to create a blockage of flow around catheter 10.

Figure 6:
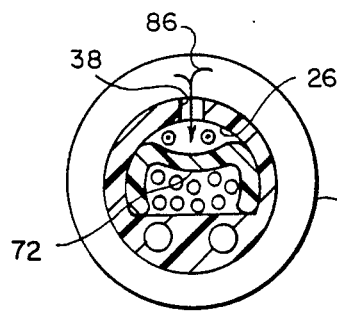
FIG. 6 is a transverse sectional view similar to that of FIG. 2, taken along the line VI—VI of FIG. 4.
Figure 4:
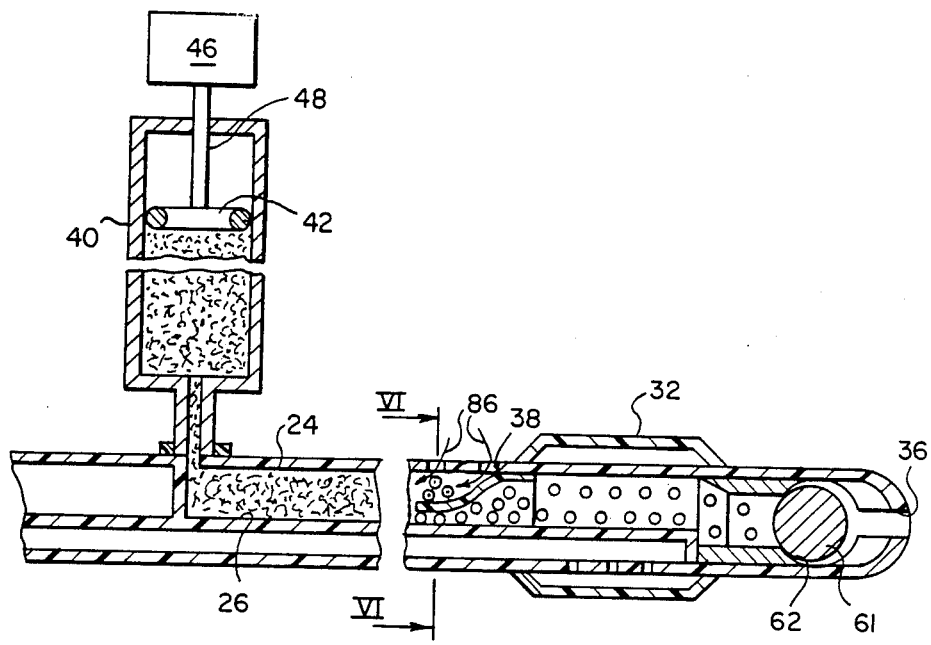
FIGS. 4 and 5 are fragmentary sectional views similar to that of FIG. 1, illustrating however the subsequent phases of the pumping operation following that shown in FIG. 3.

The next stage in the operation is to draw into the catheter, a fresh aliquot of fluid, e.g., blood, FIGS. 4 and 6. This is achieved by drawing piston 42 and rod 48 all the way to a withdrawn position, FIG. 4, so as to pull the isotonic saline solution 5 back further into tube 24. This in turn creates a differential inward pressure causing a fresh aliquot, shown as "⊙", to flow into apertures 38, arrows 86, FIGS. 4 and 6. Meanwhile ball 61 is drawn against its seat 62, thereby closing off flow into aperture 36.

Figure 3:
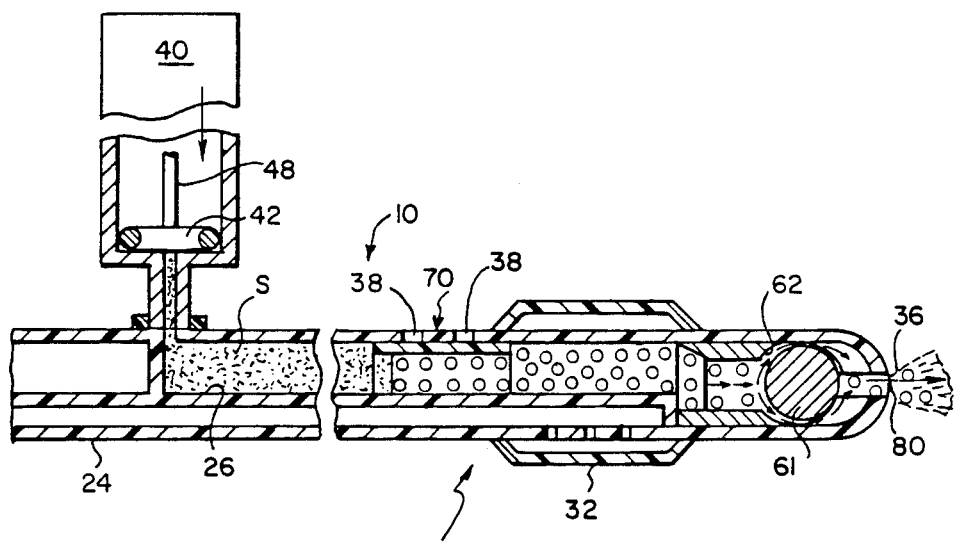
FIG. 3 is a fragmentary sectional view similar to that of FIG. 1, but illustrating one phase in the pumping operation.
Figure 5:
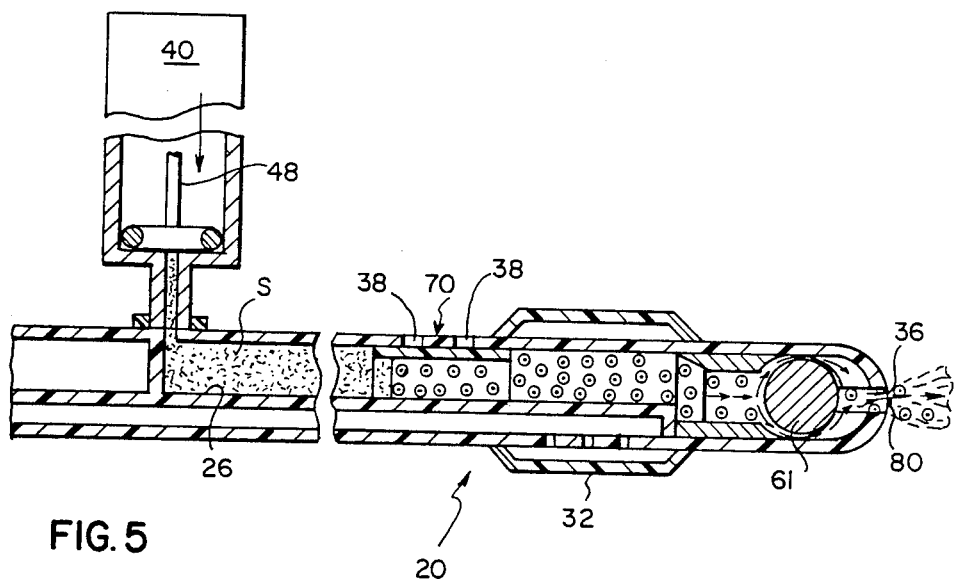

The next phase, FIG. 5, is a repetition of that shown in FIG. 3. Rod 48 advances fully, pushing saline solution S back into distal end 20. This pressure closes flap valve 70 and pushes the fresh aliquot against the remaining portions of the previous aliquot, so that both are pushed out around ball 61, arrows 80, now moved to its open position adjacent aperture 36.

Most preferably, the catheter is intended to be used in a vessel having fluid flowing in the direction of arrow 80, FIG. 5. This means it should be inserted into a body vessel, such as a vein or artery, at a location that is upstream from the site requiring treatment.

Figure 7:
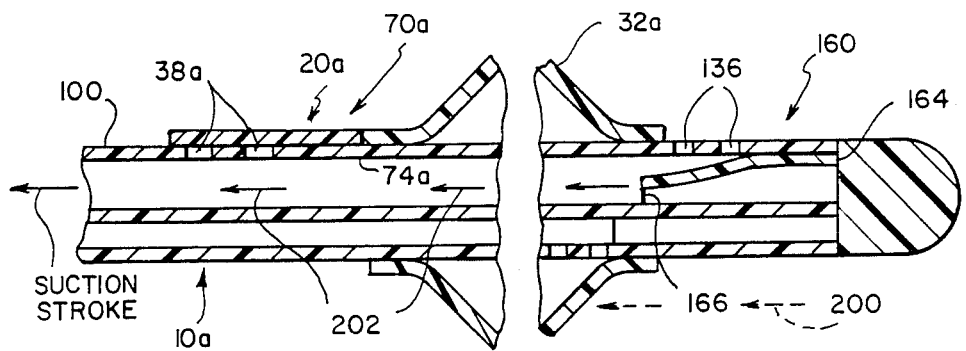
FIGS. 7 and 8 are fragmentary, longitudinal sectional views similar to a portion of that shown in FIG. 2, but of an alternate embodiment.
Figure 8:
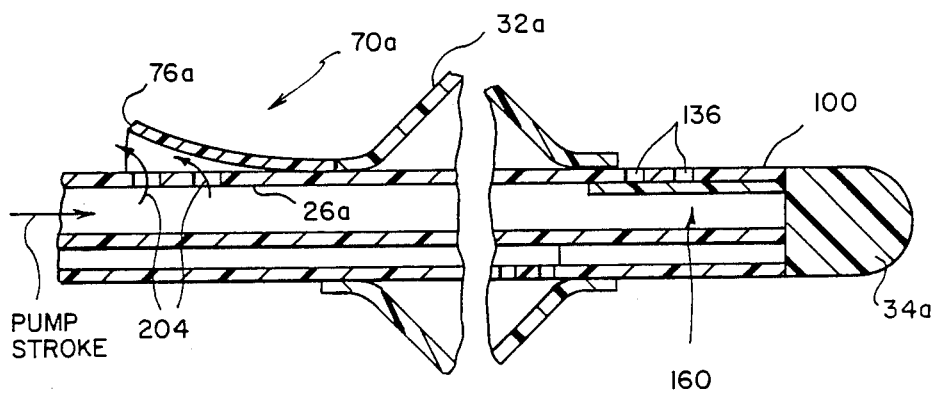

Catheter 10 can be constructed for flow delivery in the opposite direction as well, FIGS. 7-8. Parts similar to those previously described bear the same reference numeral to which the distinguishing suffix "a" has been appended.

Thus, FIGS. 7-8, catheter 10a comprises distal end 20a, and a proximal end (not shown) that is completely identical to that of FIGS. 1-6, including the pumping means. The two ends are connected by the identical tube described above. A flap valve 70a controls the flow at apertures 38a that are more proximal than balloon 32a, which balloon is identical to, and identically operated as, that previously described. Valve 160 controls flow at apertures 136 that are more distal than balloon 32a. Lumen 26a is the perfusion lumen providing communication between apertures 136 and 38a, also as in the previous embodiments.

Unlike the previous embodiments, flap valve 70a fits around the surface 100 outside of lumen 26a, to preclude flow of exterior fluid from extending into the lumen. It is securely attached at its end 74a, as before. When a differential outward pressure is developed, FIG. 8, opposite end 76a lifts off surface 100 to allow fluid to flow out of lumen 26a.

Valve 160 is constructed to be the reverse of its corresponding, distal-most valve of the previous embodiment. Valve 160 is preferably also a flap valve, constructed as a hemicylindrical tube with opposite ends 164 and 166, similar to valve 70 in the previous embodiment. End 164 is sealed around its entire circumference to lumen 26a, while end 166 is free to collapse under the pressure of entering fluid at apertures 136. If that incoming pressure is overcome with the pump pressure by pumping means 18a, FIG. 9, at proximal end 22a, then flap valve 160 closes, FIG. 8, and prevents flow out of apertures 136. Apertures 136 are located in surface 100, rather than the distal-most end 34a.

The flow "around" the obstacle created by balloon(s) 32a is thus as shown by arrow 200. That is, aliquots are drawn in the distal-most apertures 136, as shown by arrows 202, FIG. 7, and expelled out of the more proximal apertures 38a, as shown by arrows 204, FIG. 8.

Figure 9:
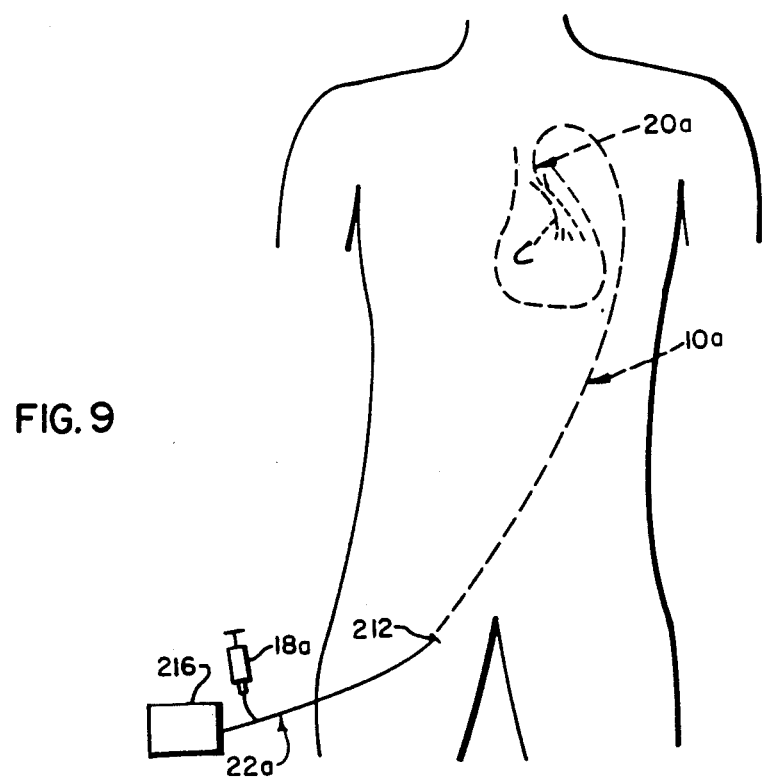
FIG. 9 is a schematic illustration of a use of a catheter constructed, as shown in Figures 7-8, to treat conditions at locations remote from the incision used to insert the catheter.

FIG. 9 illustrates the manner in which a catheter 10a constructed in accordance with the invention can be inserted in an incision 212 in a patient's body, and pushed along an artery such as the femoral artery until it reaches an occlusion, here shown as being in the coronary artery C. That occlusion is remote from the incision, as is the distal end 20a of the catheter. Control of the catheter is achieved ex vivo by conventional control means 216, located at proximal end 22 of the catheter as is conventional.

The invention has been described in detail with particular reference to preferred embodiments thereof, but it will be understood that variations and modifications can be effected within the spirit and scope of the invention.

What is claimed is:

1. In a perfusion angioplasty catheter comprising a tube having a distal end including means for effecting angioplasty treatment of a body vessel, and a proximal end containing control means, said tube further comprising at least a perfusion lumen extending most of the length of said tube, and means in said tube adjacent said distal end, defining a plurality of apertures providing for fluid movement from or to said lumen, to or from a body vessel;

the improvement wherein said catheter further comprises:
a plurality of one-way valves, each disposed at one of said apertures, at least one of said valves being constructed to admit fluid only into said lumen from a body vessel, and at least one other of said valves being constructed to admit fluid only to a body vessel from said lumen.

2. In a perfusion angioplasty catheter for insertion into a vessel of a mammalian body, said catheter comprising a distal end including treating means for effecting angioplasty treatment of a body vessel, a proximal end that remains outside of the body vessel, and a body portion extending between and connecting said ends, said distal end being provided with at least one lumen and at least one aperture on either side of said treating means, constructed to allow flow of fluid into and out of said catheter from and to, repsectively, a body vessel;

the improvement wherein said distal end further includes a plurality of one-way valves, each disposed at one of said apertures, at least one of said valves being constructed to admit fluid only into said lumen from a body vessel, and at least one other of said valves being constructed to admit fluid only to a body vessel from said lumen.

3. A catheter as defined in claim 1 or 2, and further including means for alternatively evacuating and pressurizing said lumen in at least the vicinity of said apertures, whereby fluid is alternatively drawn into said lumen and then expelled, respectively.

4. A cathter as defined in claim 3, wherein said evacuating and pressurizing means include a pump disposed adjacent to said proximal end, and wherein said pump and at least said proximal end contain an isotonic saline solution or blood substitute.

5. A catheter as defined in claim 1 or 2, and further including a balloon at said distal end and means for inflating and deflating said balloon, said at least one valve and said at least on other valve being disposed on opposite longitudinal sides of said balloon,
whereby said valves permit fluid of a body vessel to be pumped around the balloon when it is expanded to fill the body vessel.

6. A catheter as defined in claim 1 or 2, wherein at least said at least one valve is a flap valve completely covering said aperture when fluid attempts to exit said lumen at said aperture.

7. A catheter as defined in claim 6, wherein said flat vlve is mounted on the inside of said perfusion lumen.

8. A catheter as defining in claim 6, and further wherein all of said valves are flap valves, said at least one other valve being mounted on the outside of said lumen.

9. A catheter as defined in claim 1 or 2, wherein said at least one other valve is a ball valve comprising a ball and a seat positioned to close said valve with said ball against flow into said lumen.

10. A catheter as defined in claim 1 or 2, wherein said at least one valve is located upstream of said treating means measured by flow in the body vessel when said catheter is in position for use, and said at least one other valve is located downstream of said treating means.

11. In a perfusion angioplasty catheter for insertion into a vessel of a mammalian body, said catheter comprising a distal end including treating means for effecting angioplasty treatment of a body vessel, a proximal end that remains outside of the body vessel, and a body portion extending between and connecting said ends;
the improvement wherein said catheter includes means for drawing fluid into the catheter from the body vessel only at locations in said distal end that are upstream of said treating means when the catheter is in place in a body vessel, means for expelling fluid from the catheter under pressure in excess of approximately 120 mm of Hg only at locations in said distal end that are downstream of said treating means when the catheter is in place in a body vessel; and means for transferring indrawn fluid from said upstream locations to said downstream locations and to the exterior of the catheter, without withdrawing said indrawn fluid out of the body vessel from which the fluid was taken.

* * * * *

UNITED STATES PATENT AND TRADEMARK OFFICE
CERTIFICATE OF CORRECTION

PATENT NO. : 4,857,054
DATED : August 15, 1989
INVENTOR(S) : Jeffrey L. Helfer

It is certified that error appears in the above-identified patent and that said Letters Patent is hereby corrected as shown below:

Col. 7, lines 13-14, the part reading:

"said flat vlve is mounted"

should read:

--said flap valve is mounted--;

Col. 7, line 15, the part reading:

"A catheter as defining in"

should read:

--A catheter as defined in--.

Signed and Sealed this

Thirty-first Day of July, 1990

Attest:

HARRY F. MANBECK, JR.

*Attesting Officer*  *Commissioner of Patents and Trademarks*